US00PP35052P2

(12) United States Plant Patent
van den Hoogen

(10) Patent No.: US PP35,052 P2
(45) Date of Patent: Mar. 21, 2023

(54) ***VERONICA* PLANT NAMED 'ALLVENJDER'**

(50) Latin Name: ***Veronica longifolia* X *Veronica spicata***
Varietal Denomination: Allvenjder

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 17/903,476

(22) Filed: Sep. 6, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68
See application file for complete search history.

*Primary Examiner* — Anne Marie Grunberg
(74) *Attorney, Agent, or Firm* — C. Anne Whealy

(57) ABSTRACT

A new and distinct cultivar of *Veronica* plant named 'Allvenjder', characterized by its upright plant habit; moderately vigorous growth habit and moderate growth rate; freely basal branching habit; dark green-colored leaves; freely flowering habit; long and dense inflorescences with numerous light pinkish purple-colored flowers; and good performance as a garden plant and cut flower.

2 Drawing Sheets

Figure 1:
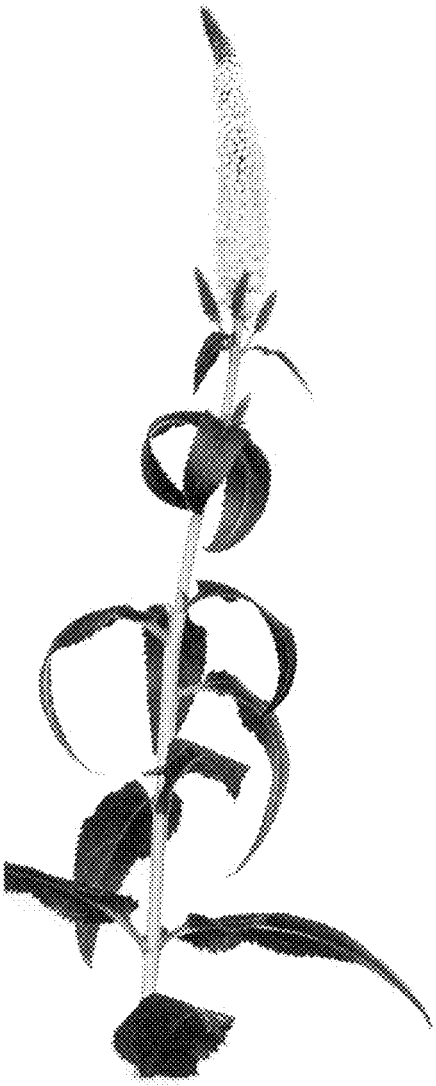

Botanical designation: *Veronica longifolia* X *Veronica spicata.*

Cultivar denomination: 'ALLVENJDER'.

PRIOR DISCLOSURES BY INVENTOR/APPLICANT & ASSIGNEE

An European Community Plant Breeder's Rights application for the instant plant was filed by the Assignee, Allplants Holding B.V. of Cuijk, The Netherlands on Nov. 19, 2021, application number 2021/2986. Foreign priority is not claimed to this application.

BACKGROUND OF THE INVENTION

The present invention relates to a new and distinct cultivar of *Veronica* plant, botanically known as *Veronica longifolia* X *Veronica spicata*, typically grown as a garden plant or cut flower and hereinafter referred to by the name 'Allvenjder'.

The new *Veronica* plant is a product of a planned breeding program conducted by the Inventor in Cuijk, The Netherlands. The objective of the breeding program is to create new attractive *Veronica* plants with attractive flowers arranged on long inflorescences and good garden performance and cut flower potential.

The new *Veronica* plant originated from an open-pollination in June, 2014 of a proprietary selection of *Veronica longifolia* X *Veronica spicata* identified as code number 1-2013-65-4, not patented, as the female, or seed, parent with an unknown selection of *Veronica longifolia* X *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in June, 2015.

Asexual reproduction of the new *Veronica* plant by terminal stem cuttings in a controlled environment in Cuijk, The Netherlands, since September, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvenjder'. These characteristics in combination distinguish 'Allvenjder' as a new and distinct *Veronica* plant:

1. Upright plant habit.
2. Moderately vigorous growth habit and moderate growth rate.
3. Freely basal branching habit.
4. Dark green-colored leaves.
5. Freely flowering habit.
6. Long and dense inflorescences with numerous light pinkish purple-colored flowers.
7. Good performance as a garden plant and cut flower.

Plants of the new *Veronica* differ primarily from plants of the female parent selection primarily in flower color as plants of the new *Veronica* have light pinkish purple-colored flowers whereas plants of the female parent selection have blue-colored flowers. Additionally, inflorescences of plants of the new *Veronica* are long and narrowly columnar whereas inflorescences of plants of the female parent selection are slightly cristata-shaped.

Plants of the new *Veronica* can be compared to plants of *Veronica longifolia* X *Veronica spicata* 'Allenjoyce', not patented. In side-by-side comparisons, plants of the new *Veronica* differ primarily from plants of 'Allenjoyce in flower color as plants of the new *Veronica* have lighter pinkish purple-colored flowers than plants of 'Allenjoyce'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering stem of 'Allvenjder'.

Figure 3:
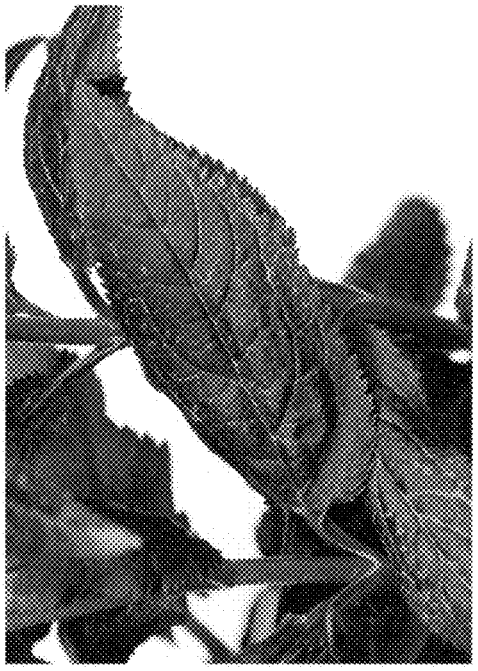
Figure 2:
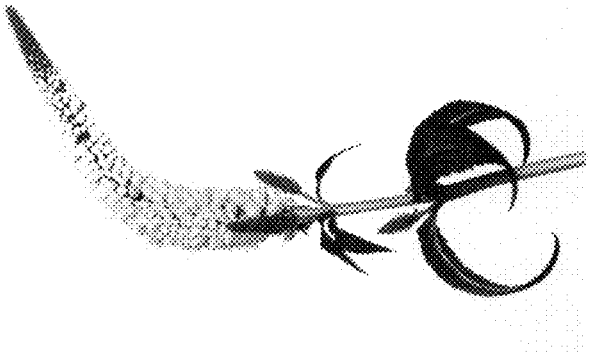

The photographs on the second sheet are close-up views of a typical inflorescence (FIG. 2) and typical leaves (FIG. 3) of 'Allvenjder'.

DETAILED BOTANICAL DESCRIPTION

Plants used for the aforementioned photographs and following description were grown in ground beds during the autumn and winter initially in an outdoor nursery and then in a glass-covered greenhouse for the last five weeks of production in Cuijk, The Netherlands and under cultural practices typical of commercial *Veronica* production. During the production of the plants, day temperatures ranged from 20° C. to 28° C. and night temperatures ranged from 2° C. to 15° C. Plants were one year old when the photographs and the description were taken. In the following description, color references are made to The Royal Horticultural Society Colour Chart, 2015 Edition, except where general terms of ordinary dictionary significance are used.

Botanical classification: *Veronica longifolia* X *Veronica spicata* 'Allvenjder'.

Parentage:

- *Female, or seed, parent*.—Proprietary selection of *Veronica longifolia* X *Veronica spicata* identified as code number 1-2013-65-4, not patented.
- *Male, or pollen, parent*.—Unknown selection of *Veronica longifolia* X *Veronica spicata*, not patented.

Propagation:

- *Type cutting*.—Terminal stem cuttings.
- *Time to initiate roots, summer*.—About 10 to 14 days at temperatures ranging from 12° C. to 30° C.
- *Time to produce a rooted young plant, summer*.—About 24 to 32 days at temperatures ranging from 12° C. to 30° C.
- *Root description*.—Fine, fleshy; typically white in color, actual color of the roots is dependent on substrate composition, water quality, fertilizer type and formulation, substrate temperature and physiological age of roots.
- *Rooting habit*.—Freely branching; dense.

Plant description:

- *Plant type*.—Herbaceous perennial.
- *Plant and growth habit*.—Upright plant habit with long and dense inflorescences; overall plant shape, oblong to narrowly oblong; moderately vigorous growth habit and moderate growth rate.
- *Plant height, soil level to top of foliar plane*.—About 49.6 cm.
- *Plant height, soil level to top of floral plane*.—About 58 cm.
- *Plant width*.—About 26.9 cm.
- *Lateral branch description*.—Branching habit: Freely basal branching habit with about six primary stems per plant each with about two secondary branches; pinching will enhance lateral branching. Length (excluding inflorescence): About 45.1 cm. Diameter: About 4 mm. Internode length: About 4.9 cm. Strength: Strong. Aspect: Erect to about 10° from vertical. Texture and luster: Densely pubescent; slightly glossy. Color, developing: Close to 146B. Color, developed: Close to a blend of 144A and 144B.

Leaf description:

- *Arrangement*.—Opposite or in whorls of three, simple.
- *Length*.—About 8.1 cm.
- *Width*.—About 3.9 cm.
- *Shape*.—Ovate to narrowly ovate; curled downwardly.
- *Apex*.—Acute to narrowly acute.
- *Base*.—Truncate.
- *Margin*.—Serrate; not lobed.
- *Texture and luster, upper surface*.—Moderately pubescent; slightly rugose; slightly glossy.
- *Texture and luster, lower surface*.—Smooth, glabrous with exception of midvein which is moderately pubescent; not rugose; slightly glossy.
- *Venation pattern*.—Pinnate.
- *Color*.—Developing leaves, upper surface: Close to 137B. Developing leaves, lower surface: Close to 138A. Fully expanded leaves, upper surface: Close to NN137A; venation, close to 138A. Fully expanded leaves, lower surface: Close to 147B; venation, close to 144A.
- *Petioles*.—Length: About 1.4 cm. Diameter: About 3 mm by 3 mm. Strength: Strong. Texture and luster, upper surface: Moderately to densely pubescent; slightly glossy. Texture and luster, lower surface: Smooth, glabrous; slightly glossy. Color, upper and lower surfaces: Close to a blend of 144A and 144B.

Flower description:

- *Flower arrangement and shape*.—Single campanulate flowers arranged on long and dense terminal racemes; flowers face mostly outwardly.
- *Flowering habit*.—Freely flowering habit with about 500 flowers developing per inflorescence and about 4,500 flowers developing per plant during the flowering season.
- *Fragrance*.—None detected.
- *Natural flowering season*.—Long flowering period; plants flower continuously from the summer until the autumn in The Netherlands; plants begin flowering about 13 weeks after planting.
- *Flower longevity*.—Individual flowers last about seven days; inflorescences last about three weeks on the plant and about two weeks as a cut flower; flowers not persistent.
- *Flower buds*.—Length: About 4 mm. Diameter: About 2 mm. Shape: Ovate. Texture and luster: Smooth, glabrous; matte. Color: Close to 77D and towards the base, close to 76D; developing calyx, close to 138A.
- *Inflorescence height* (*length*).—About 8.4 cm.
- *Inflorescence diameter*.—About 1.6 cm.

*Flower diameter*.—About 5 mm by 5 mm.

*Flower length*.—About 7 mm.

*Throat diameter*.—About 3 mm.

*Tube length*.—About 2 mm.

*Tube diameter*.—About 2.5 mm.

*Petals*.—Quantity and arrangement: Five in a single whorl; two upper petals larger than three lower petals; petals fused about 40% of the petal length from the base. Length, upper petals: About 5 mm. Length, lower petals: About 4.5 mm. Width, upper petals: About 2.5 mm. Width, lower petals: About 2.25 mm. Shape, all petals: Obovate; concave. Apex, all petals: Obtuse. Margin, all petals: Entire; not undulate. Texture and luster, all petals, upper and lower surfaces: Smooth, glabrous; not rugose; matte. Texture and luster, throat: Smooth, glabrous; matte. Texture and luster, tube: Moderately pubescent; matte. Color, all petals: When opening, upper and lower surfaces: Close to N75D. Fully opened, upper surface: Close to 76B; venation, close to 76B; color becoming closer to 76C to lighter than 76C with subsequent development. Fully opened, lower surface: Close to 76B; venation, close to 76B; color does not change with subsequent development. Throat: Close to 76C to lighter than 76C; venation, close to 76C to lighter than 76C. Tube: Close to NN155C; venation, close to NN155C.

*Sepals*.—Quantity and arrangement: Four arranged in a single whorl and fused at the base. Length: About 1.75 mm. Width: About 0.75 mm. Shape: Narrowly ovate. Apex: Acute. Base: Broadly cuneate, fused. Margin: Entire. Texture and luster, upper and lower surfaces: Smooth, glabrous; matte. Color: When opening and fully opened, upper surface: Close to 137A. When opening and fully opened, lower surface: Close to 138A.

*Peduncles*.—Length: About 9.5 cm. Diameter: About 2.5 mm. Aspect: Primary peduncles, upright; secondary peduncles, about 20° from main peduncle axis. Strength: Strong. Texture and luster: Moderately pubescent; slightly glossy. Color: Close to 143B.

*Pedicels*.—Length: About 1 mm. Diameter: About 0.5 mm. Aspect: About 60° from peduncle axis. Strength: Moderately strong. Texture and luster: Moderately pubescent; slightly glossy. Color: Close to a blend of 144A and 144B.

*Flower bracts*.—None observed.

*Reproductive organs*.—Stamens: To date, stamen development has not been observed on plants of the new *Veronica*. Pistils: Quantity per flower: If present, one. Pistil length: About 5.5 mm. Stigma diameter: About 2 mm. Stigma shape: Club-shaped. Stigma color: Close to N81D. Style length: About 5.25 mm. Style color: Close to N81C. Ovary color: Close to 143B.

*Seeds and fruits*.—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'Allvenjder' as illustrated and described.

* * * * *